(12) United States Patent
Dan et al.

(10) Patent No.: US 9,332,760 B2
(45) Date of Patent: May 10, 2016

(54) WET HAND TOWEL AND METHOD FOR PRODUCING THE SAME

(71) Applicant: VB JAPAN TECHNOLOGY CO., LTD., Kunitachi-shi, Tokyo (JP)

(72) Inventors: Katsuaki Dan, Kashiwa (JP); Toshihiro Yamase, Yokohama (JP); Hiromichi Ichikawa, Higashimatsuyama (JP)

(73) Assignee: VB JAPAN TECHNOLOGY CO., LTD., Tokyo (JP)

( * ) Notice: Subject to any disclaimer, the term of this patent is extended or adjusted under 35 U.S.C. 154(b) by 0 days.

(21) Appl. No.: 14/372,375

(22) PCT Filed: Jan. 24, 2013

(86) PCT No.: PCT/JP2013/051470
§ 371 (c)(1),
(2) Date: Jul. 15, 2014

(87) PCT Pub. No.: WO2013/115061
PCT Pub. Date: Aug. 8, 2013

(65) Prior Publication Data
US 2014/0363520 A1 Dec. 11, 2014

(30) Foreign Application Priority Data

Jan. 31, 2012 (JP) .................. 2012-017500

(51) Int. Cl.
| | | |
|---|---|---|
| *A01N 43/90* | (2006.01) | |
| *A01N 31/16* | (2006.01) | |
| *D06M 13/156* | (2006.01) | |
| *D06M 11/36* | (2006.01) | |
| *D06M 11/56* | (2006.01) | |
| *D06M 13/418* | (2006.01) | |
| *D06M 16/00* | (2006.01) | |
| *A01N 59/16* | (2006.01) | |
| *A01N 25/34* | (2006.01) | |
| *B05D 7/24* | (2006.01) | |
| *A61K 31/431* | (2006.01) | |
| *A61K 8/02* | (2006.01) | |
| *A61K 31/085* | (2006.01) | |
| *A61K 33/24* | (2006.01) | |
| *A61K 8/34* | (2006.01) | |
| *A61K 8/49* | (2006.01) | |
| *A61Q 19/10* | (2006.01) | |
| *A61K 8/19* | (2006.01) | |
| *A61K 8/23* | (2006.01) | |

(52) U.S. Cl.
CPC ............. *A01N 43/90* (2013.01); *A01N 25/34* (2013.01); *A01N 31/16* (2013.01); *A01N 59/16* (2013.01); *A61K 8/0208* (2013.01); *A61K 8/19* (2013.01); *A61K 8/23* (2013.01); *A61K 8/347* (2013.01); *A61K 8/49* (2013.01); *A61K 31/085* (2013.01); *A61K 31/431* (2013.01); *A61K 33/24* (2013.01); *A61Q 19/10* (2013.01); *B05D 7/24* (2013.01); *D06M 11/36* (2013.01); *D06M 11/56* (2013.01); *D06M 13/156* (2013.01); *D06M 13/418* (2013.01); *D06M 16/00* (2013.01); *A61K 2800/242* (2013.01)

(58) Field of Classification Search
None
See application file for complete search history.

(56) References Cited

U.S. PATENT DOCUMENTS

| | | | |
|---|---|---|---|
| 4,111,844 A | 9/1978 | Polony et al. | |
| 6,565,890 B2 * | 5/2003 | Shigeta et al. | ............... 424/600 |
| 2003/0039702 A1 | 2/2003 | Shigeta et al. | |
| 2009/0259157 A1 * | 10/2009 | Thomas | .......................... 602/48 |
| 2011/0105976 A1 * | 5/2011 | Berlin | ............................ 602/48 |

FOREIGN PATENT DOCUMENTS

| | | |
|---|---|---|
| JP | A-2000-229864 | 8/2000 |
| JP | A-2005-298374 | 10/2005 |
| JP | A-2005-325083 | 11/2005 |
| JP | A-2006-273837 | 10/2006 |
| JP | 2006340949 | * 12/2006 |
| JP | A-2008-119433 | 5/2008 |
| JP | A-2009-149575 | 7/2009 |
| JP | A-2010-022606 | 2/2010 |
| JP | A-2010-229108 | 10/2010 |
| WO | WO 2005/110443 | * 11/2005 |

OTHER PUBLICATIONS

Shigeta et al. "Broad Spectrum anti-RNA virus activities of titanium and vanadium substituted polyoxotungates".*
Yamase, "Anti-tumor, -viral, and -bacterial activities of polyoxometalates for realizing an inorganic drug," *Journal of Materials Chemistry*, Jul. 19, 2005, pp. 4773-4782, vol. 15.
Aug. 5, 2014 International Preliminary Report on Patentability issued in International Application No. PCT/JP2013/051470.
Mar. 19, 2013 International Search Report issued in International Patent Application No. PCT/JP2013/051470 (with translation).
Jul. 6, 2015 Extended European Search Report issued in European Patent Application No. EP13743291.0.

* cited by examiner

*Primary Examiner* — Robert A Wax
*Assistant Examiner* — Danah Al-Awadi
(74) *Attorney, Agent, or Firm* — Oliff PLC (57) ABSTRACT

A substrate contains a composition including $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol.

3 Claims, 3 Drawing Sheets

WET HAND TOWEL AND METHOD FOR PRODUCING THE SAME

TECHNICAL FIELD

The present invention relates to a wet hand towel (Oshibori) which contains a composition having an antibacterial activity and antiviral activity, and a method for producing the wet hand towel.

BACKGROUND ART

As a wet hand towel (Oshibori), a wet hand towel for rent based on a fiber product such as towel, or a disposable wet hand towel based on paper or nonwoven fabric is mainly known. Depending on an environment for use or storage of a wet hand towel, bacteria or viruses may attach to and grow in the wet hand towel.

Against such bacteria or viruses, the use of paraben or highly-concentrated alcohol is considered, which may cause skin surface roughening. Accordingly, Patent Literature 1 discloses a disposable wet hand towel which has an antifungal effect with the use of an aqueous solution including ε-polylysine and an alkali metal salt of sorbic acid.

CITATION LIST

{Patent Literature}
Patent Literature 1: JP 2009-149575 A

SUMMARY OF INVENTION

Technical Problem

However, because the disposable wet hand towel of Patent Literature 1 may allow various kinds of bacteria and viruses to attach to and grow in the wet hand towel depending on environments for use and storage, it is desirable to have an antibacterial activity against various kinds of bacteria and an antiviral activity against various kinds of viruses.

In addition, a wet hand towel for rent is used in a rental destination such as a restaurant, showroom, office and beauty parlor, in which the wet hand towel is offered to a user. After the wet hand towel for rent has been used, the wet hand towel will be recovered and washed, followed by reused. In regards to the washing, the "Guideline for sanitary treatment of wet hand towel etc." from the Ministry of Health, Labor and Welfare requires that the number of bacterium after the washing should be equal to or less than the standard value.

However, a wet hand towel for rent is used in so various environments that various kinds of bacteria or viruses may attach to and propagate in the wet hand towel for rent. Accordingly, it is required that such a wet hand towel for rent have an antibacterial activity against not only a specific bacterium but also various kinds of bacteria, and an antiviral activity against not only a specific virus but also various kinds of viruses.

Here, for the purpose of acquiring a composition which has an antibacterial activity against various kinds of bacteria and an antiviral activity against various kinds of viruses, it is considered that a plurality of compounds are combined, each of which has an antibacterial activity against a specific bacterium or an antiviral activity against a specific virus. However, when the plurality of compounds are randomly selected to be combined, the combined compounds often react to each other or inhibit the individual antibacterial activity or antiviral activity. Therefore, it is difficult to acquire such a composition which has an antibacterial activity against various kinds of bacteria and an antiviral activity against various kinds of viruses.

An object of the present invention is to provide a wet hand towel (Oshibori) having an antibacterial activity against various kinds of bacteria and an antiviral activity against various kinds of viruses, and a method for producing a wet hand towel.

Solution to Problem

As a result of earnest investigation by the inventors, it has been found that when a specific metal oxide cluster compound, a specific antibiotic substance and a specific antibacterial agent are selected, these selected compounds do not react to each other, nor inhibit the antibacterial activities or antiviral activities the individual compounds have, and thus the present invention has been completed.

According to the present invention, a wet hand towel (Oshibori) has a substrate containing a composition including $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol.

According to the present invention, a method for producing a wet hand towel (Oshibori), includes the steps of: preparing a substrate; and allowing the substrate to contain a composition comprising $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol.

According to the present invention, the method for producing a wet hand towel (Oshibori) includes the step of washing the substrate, wherein the step of washing is performed before the step of allowing to contain.

Advantageous Effects of Invention

According to the present invention, a wet hand towel having an antibacterial activity against various kinds of bacteria and an antiviral activity against various kinds of viruses, and a method for producing a wet hand towel can be provided.

DESCRIPTION OF EMBODIMENTS

Hereinafter, a description is made of a wet hand towel (Oshibori) and a method for producing a wet hand towel according to the present invention with reference to the drawings. According to the present invention, a wet hand towel has a substrate containing a composition including $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol. As a substrate of the wet hand towel according to the present invention, a towel, nonwoven fabric, paper or the like may be used. As a material of the towel, cotton or the like is used. In addition, allowing the substrate to contain a predetermined amount or more of water may result in the wet hand towel.

Hereinafter, a description is made of a method for producing a wet hand towel according to a first embodiment of the present invention. In the wet hand towel of this embodiment, a towel is mainly used as a substrate. In addition, the wet hand towel of this embodiment is a so-called wet hand towel for rent, that is a towel is used in a rental destination and then the used towel is recovered. Moreover, washing the wet hand towel according to this embodiment is performed so as to fulfill the "Guideline for sanitary treatment of wet hand towel etc." from the Ministry of Health, Labor and Welfare.

Figure 1:
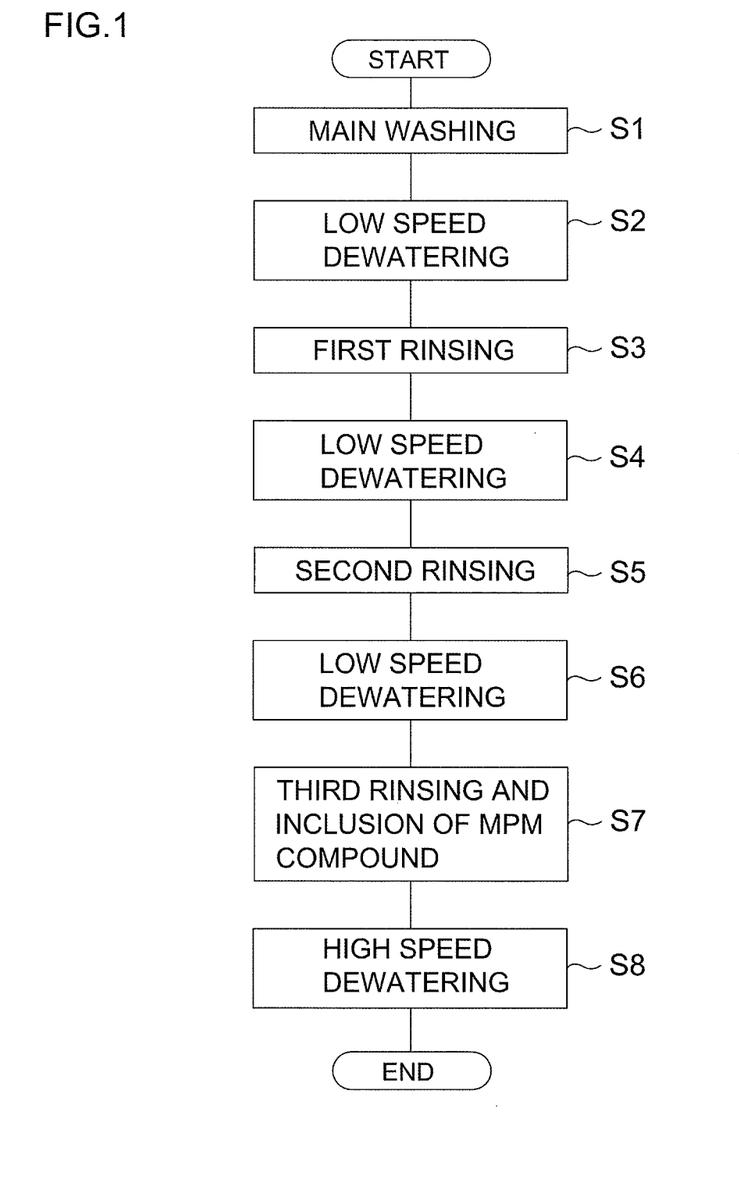
FIG. 1 is a flowchart that illustrates a process for producing a wet hand towel according to a first embodiment of the present invention.

FIG. 1 is a flowchart that illustrates a process for producing the wet hand towel according to the first embodiment. Main washing is performed in which in a cleaning tank of a laundry machine are put the towel that has been used in a restaurant or the like and then recovered, and a detergent (step S1), followed by low speed dewatering for a predetermined period of time (step S2). Here, the main washing is performed under a middle water level for a predetermined period of time equal to or more than 10 minutes at a predetermined temperature (equal to or more than 60° C.).

Subsequently, first rinsing is performed for a predetermined period of time at a predetermined temperature in which the water level in the cleaning tank is brought high with the use of clean water (step S3), followed by low speed dewatering for a predetermined period of time (step S4). Furthermore, second rinsing is performed for a predetermined period of time at a predetermined temperature in which the water level in the cleaning tank is brought high with the use of clean water, along with a bleaching powder or sodium hypochlorite is added therein so that the free chlorine level reaches 250 ppm (step S5), followed by low speed dewatering for a predetermined period of time (step S6).

Thereafter, third rinsing is performed for a predetermined period of time at a predetermined temperature in which the water level in the cleaning tank is brought middle with the use of clean water, along with an MPM composition is added therein (step S7).

Here, the MPM composition is formulated from $VOSO_4$, $K_{11}H[(VO)_3(SbW_9O_{33})_2]$, $Na_9[SbW_9O_{33}]$, oxacillin and irgasan (systematic name: 5-chloro-2-(2,4-dichlorophenoxy) phenol) at a predetermined ratio. Here, the compounding ratio of these compounds is not particularly limited, but in the MPM composition are included $VOSO_4$ of preferably 0.1 to 20 mol, more preferably 4 to 8 mol, $Na_9[SbW_9O_{33}]$ of preferably 0.1 to 30 mol, more preferably 10 to 20 mol, oxacillin of preferably 0.1 to 30 mol, more preferably 5 to 15 mol, and irgasan of preferably 1 mol or less, more preferably 0.2 mol or less, with respect to $K_{11}H[(VO)_3(SbW_9O_{33})_2]$ of 1 mol.

In addition, it is particularly preferable that $VOSO_4$, $K_{11}H[(VO)_3(SbW_9O_{33})_2]$, $Na_9[SbW_9O_{33}]$ and oxacillin be used at a molar ratio of 5.5:1:17.3:12.5 in the order. Moreover, it is particularly preferable that the compounding amount of irgasan be less than each of the compounding amounts of the other four compounds, for example the compounding amount of irgasan being around 10% of $K_{11}H[(VO)_3(SbW_9O_{33})_2]$ at a molar ratio.

$VOSO_4$, $K_{11}H[(VO)_3(SbW_9O_{33})_2]$ and $Na_9[SbW_9O_{33}]$, which constitute the MPM composition, are compounds belonging to a metal oxide cluster, called polyoxometalates (PM compounds). Here, the PM compounds are metal oxide cluster compounds having polyacid ions, and each of the compounds belonging to the PM compounds has its own bioactivity such as an antibacterial activity and antiviral activity, as disclosed in Literature 2 (Journal of Materials Chemistry, volume 15, pages 4773 to 4782, 2005, Royal Society of Chemistry). Note that a poly acid means a metal oxide cluster compound constituted by a transition metal element (such as W(VI) and V(V)), which has a structure in which typically 4 or 6 oxygen atoms are coordinated to a metal atom or the like to form a tetrahedron or octahedron as a basic unit, and the basic units couple with each other through their edges or peak points.

Oxacillin is an antibiotic substance exhibiting an activity against bacteria such as *Staphylococcus aureus*, as well as a compound showing an activity against viruses such as influenza virus. When oxacillin is formulated with the PM compound, the antibacterial activity obtained can be higher than that obtained in case where oxacillin is used alone. In addition, irgasan is a compound having an antibacterial activity against common bacteria.

When the MPM composition is dissolved in water for use as an aqueous solution, the MPM aqueous solution should be prepared such that each of the compounds which constitute the MPM composition has a minimum effective concentration or higher. The compounds of $VOSO_4$, $K_{11}H[(VO)_3(SbW_9O_{33})_2]$, $Na_9[SbW_9O_{33}]$, oxacillin and irgasan, which constitute the MPM composition, have the concentrations in the MPM aqueous solution preferably from 1 to 50, from 10 to 300, from 50 to 1500, from 5 to 200 and from 0.01 to 3 µg/mL, respectively, more preferably from 20 to 40, from 50 to 150, from 500 to 1300, from 50 to 200, and from 0.1 to 1 µg/mL, respectively. In addition, the compounds of $VOSO_4$, $K_{11}H[(VO)_3(SbW_9O_{33})_2]$, $Na_9[SbW_9O_{33}]$, oxacillin and irgasan, which constitute the MPM composition, have the concentrations in the MPM aqueous solution particularly preferably of 25, 115, 1000, 100 and 0.6 µg/mL, respectively.

In addition, as long as the MPM composition is at 100° C. or lower, that is the aqueous solution as the MPM composition does not boil, the MPM composition can maintain the antibacterial activity and antiviral activity, and such activities are relatively stable even when temperature is raised. The compounds which constitute the MPM composition do not react to each other, nor inhibit the antibacterial activities or antiviral activities the individual compounds have. Moreover, they are safe compounds so as not to cause skin surface roughening on the human body. Furthermore, the MPM composition is a safe compound so as not to accumulate in the human body.

After the third rinsing has been completed, high speed dewatering is performed for a predetermined period of time (step S8). This step allows the towel to contain a predetermined amount of water and further the MPM composition. In addition, after allowing the towel to contain the MPM composition, forming the towel into a predetermined shape will result in the wet hand towel of the present invention. Here, the forming the towel into the predetermined shape can be achieved through folding or winding up the towel. In addition, after the towel is formed into a predetermined shape, the towel may be wrapped with a film or the like.

The discharged water including the MPM composition and the like drained from the cleaning tank is collected in a treatment tank that performs a discharged water treatment by a microbiological treatment method.

According to this first embodiment, it is possible to produce the wet hand towel having an antibacterial activity against various kinds of bacteria and an antiviral activity against various kinds of viruses. In addition, with the use of an aqueous solution rather than an organic solvent, and with the use of the MPM composition, it is also possible to prevent the effect on the human body, such as skin surface roughening.

In addition, it is also possible for the wet hand towel to contain at a low cost a composition having an excellent antibacterial activity and excellent antiviral activity. Furthermore, the MPM composition has also an antifungal effect, and thus it is possible for the wet hand towel to contain at a low cost a composition having an antifungal effect. Moreover, the discharged water including the MPM composition does not have such an adverse effect on microorganisms (bacteria) as to deaden them in the treatment tank that performs a microbiological treatment method.

Note that, although in the above-mentioned first embodiment, the MPM composition is contained in a towel during the third rinsing, the MPM composition may be contained in a towel during any of the steps as long as the MPM composition can be contained in the towel. For example, the MPM composition may be contained into a towel during the first rinsing or the second rinsing, or alternatively a towel may be immersed in the MPM aqueous solution inside a towel dipping tank after the high speed dewatering, in such a way as step S21 in FIG. 2 as described below, thereby the MPM aqueous solution infiltrating into the towel. In addition, a towel may be formed into a predetermined shape, and then sprayed with the MPM aqueous solution or the like, thereby the MPM composition being contained in the towel.

Next, a description is made of a method for producing a wet hand towel according to a second embodiment of the present invention. Note that in the method for producing a wet hand towel according to this second embodiment, instead of a recovered towel used as a substrate in the first embodiment, a new towel is used. Accordingly, the same detailed description is omitted as that of the first embodiment, but a detailed description is made of only a different part.

Figure 2:
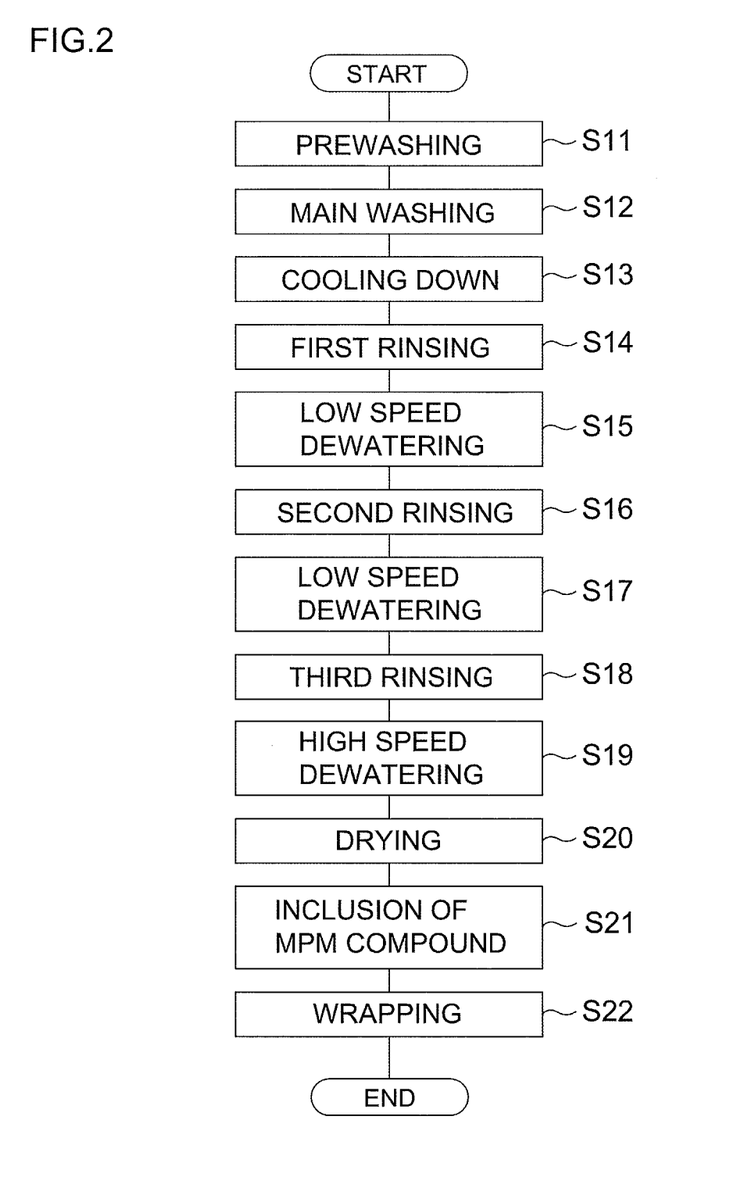
FIG. 2 is a flowchart that illustrates a process for producing a wet hand towel according to a second embodiment of the present invention.

A new towel is put into a cleaning tank, and prewashing is performed under a predetermined water level for several minutes at a predetermined temperature without the drum being rotated (step S11). Then, a desizing agent and a refining and penetrating agent are put therein, and main washing is performed under a predetermined water level for a predetermined period of time equal to or more than 10 minutes at a predetermined temperature such as 80° C. (step S12), followed by cooling down for a predetermined period of time at a predetermined temperature such as 60° C. (step S13).

Then, rinsing and low speed dewatering are performed, as indicated in step S14 to step S17, in which the treatments are the same as those indicated in step S3 to step S6 in the flow chart of FIG. 1, respectively, so the description thereof is omitted.

Thereafter, third rinsing is performed for a predetermined period of time at a predetermined temperature in which the water level in the cleaning tank is brought to a predetermined level with the use of clean water, along with Niccanon (made by Nicca Chemical Co., Ltd.) is added to reach 1 g/L (step S18), followed by high speed dewatering for a predetermined period of time (step S19).

Then, the towel that has undergone the high speed dewatering is taken out of the cleaning tank, and the towel is dried for a predetermined period of time at 80° C. in a drying machine (step 20). Thereafter, the towel is allowed to contain the above-mentioned MPM composition (step S21). Here, examples of the method for allowing to contain the MPM composition may include, but not particularly limited to, a method for immersing a towel in an aqueous solution in which the MPM composition is dissolved, or a method for spraying to a towel the aqueous solution in which the MPM composition is dissolved.

When the towel is immersed, for example, clean water and the MPM composition are put in a towel dipping tank that has a stirring function, and then stirred to form the aqueous solution in which the MPM composition is dissolved (the MPM aqueous solution), and subsequently the towel taken out of the cleaning tank is put in the towel dipping tank to be immersed. At this time, the compounds of $VOSO_4$, $K_{11}H[(VO)_3(SbW_9O_{33})_2]$, $Na_9[SbW_9O_{33}]$, oxacillin and irgasan, which constitute the MPM composition, have the concentrations in the MPM aqueous solution preferably of at least 25, 115, 1000, 100 and 0.6 µg/mL, respectively. In addition, the towel may be immersed with the use of a crane equipped with a jig for immersing a towel. Moreover, the towel may be immersed in the MPM aqueous solution with the aid of a buoyancy preventing weight attached to the towel. After the MPM aqueous solution has sufficiently infiltrated into the towel in the towel dipping tank, the towel is taken out of the towel dipping tank, lifted and left as it is until the MPM aqueous solution drops from the towel. Then, the towel is pressed with the use of a pressing machine for several minutes.

Then, forming into a predetermined shape the towel which has contained the MPM composition, and then wrapping with a film the towel with the use of a wrapping machine (step S22) may produce the wet hand towel according to the embodiment. Note that the moisture-vapor transmission rate of the film used in this embodiment is preferably equal to or lower than a predetermined value.

The discharged water including the MPM composition and the like drained from the cleaning tank is collected in a treatment tank that performs a discharged water treatment by a microbiological treatment method.

According to the method for producing a wet hand towel of this second embodiment, it is possible to produce the wet hand towel having an antibacterial activity against various kinds of bacteria and an antiviral activity against various kinds of viruses. In addition, with the use of an aqueous solution rather than an organic solvent, and with the use of the MPM composition, it is also possible to prevent the effect on the human body, such as skin surface roughening.

In addition, it is also possible for the wet hand towel to contain at a low cost a composition having an excellent antibacterial activity and excellent antiviral activity. Furthermore, the MPM composition has also an antifungal effect, and thus it is possible for the wet hand towel to contain at a low cost a composition having an antifungal effect. Moreover, the discharged water including the MPM composition does not have such an adverse effect on microorganisms (bacteria) as to deaden them in the treatment tank that performs a microbiological treatment method.

Note that the laundry machine is not particularly limited for use in the above-mentioned first and second embodiments. A laundry machine may be used that has one cleaning tank, a batch-type laundry machine may be used that individually performs a prewashing, main washing, rinsing and the like in a single tank, or a continuous-type laundry machine may be used that has a plurality of baths in parallel each for prewashing, main washing, rinsing and the like so as to perform laundering while moving the object to be laundered such as a towel among the baths.

In addition, the processes for producing the wet hand towel in the above-mentioned first and second embodiment are only examples, and thus may be modified appropriately depending on the type or color of the substrate.

Next, a description is made of a method for producing a wet hand towel according to a third embodiment of the present invention. Note that in the method for producing a wet hand towel according to this third embodiment, instead of a towel used as a substrate in the first embodiment, paper, nonwoven fabric or the like is used.

Figure 3:
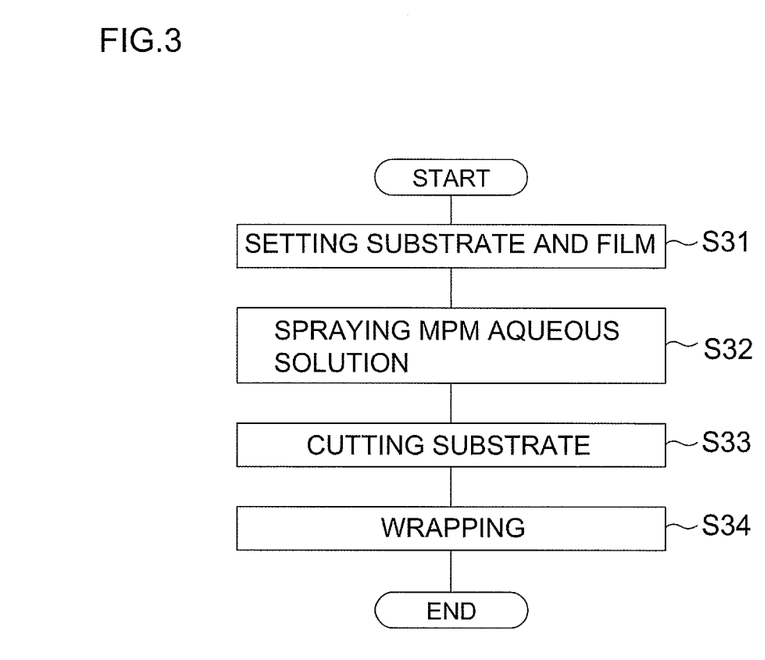
FIG. 3 is a flowchart that illustrates a process for producing a wet hand towel according to a third embodiment of the present invention.

First of all, a roll substrate made of paper or nonwoven fabrics, and a wrapping film are set on a wet hand towel producing machine (step S31). Then, the substrate is folded to a predetermined size by the wet hand towel producing machine, and the MPM aqueous solution is sprayed to the folded substrate from above and below (step S32). Thereafter, the substrate is cut to a predetermined size by a rotary cutter that the wet hand towel producing machine has (step S33), and the cut substrate is wrapped with the film (step S34), with the result that the wet hand towel of the embodiment may be produced.

According to this third embodiment, it is possible to produce the wet hand towel having an antibacterial activity against various kinds of bacteria and an antiviral activity against various kinds of viruses. In addition, with the use of an aqueous solution rather than an organic solvent, and with the use of the MPM composition, it is also possible to prevent the effect on the human body, such as skin surface roughening. In addition, it is also possible for the wet hand towel to contain at a low cost a composition having an excellent antibacterial activity and excellent antiviral activity.

In addition, because in the third embodiment paper or nonwoven fabric is used as a substrate, it is possible to produce a disposable wet hand towel having an excellent antibacterial activity and excellent antiviral activity. Furthermore, the MPM composition has also an antifungal effect, and thus it is possible for the wet hand towel to contain at a low cost a composition having an antifungal effect.

In addition, the wet hand towel produced through the method for producing a wet hand towel according to the third embodiment will satisfy the sanitary standard for a paper wet hand towel prescribed by Japan Cleansing Wipes Industry Association.

Note that the wet hand towel produced through this third embodiment may be in the form such that the substrate pieces cut to a predetermined size in step S33 are individually wrapped piece by piece, or may be in the form of so-called wet wipe such that the plurality of substrate pieces cut to a predetermined size in step S33 are stored in a package such as a bottle so as to be taken out of this package piece by piece.

In order to be taken out piece by piece, it is preferable for the substrate to be formed into a folded or rolled shape suitable to be taken out piece by piece through an output port provided through the package.

In addition, in each of the above-mentioned embodiments, the wet hand towel is allowed to contain the MPM composition, but the wet hand towel may further be allowed to contain another ingredient such as a medical agent. In this case, for example, in the third embodiment, the MPM aqueous solution is sprayed in which another medicinal solution for wet hand towel, moisturizing agent or the like has been further added. Examples of the moisturizing agent include fulvic acid, hyaluronic acid, royal jelly, glycerin and soybean extract. The MPM aqueous solution does not inhibit the effect of such another medicinal solution for wet hand towel, moisturizing agent or the like, and the antibacterial activity, antiviral activity and antifungal efficiency of the MPM aqueous solution are not also inhibited by such another medicinal solution for wet hand towel, moisturizing agent or the like.

Also, in each of the above-mentioned embodiments, the wet hand towel is allowed to contain the MPM composition, but soap such as hand soap, or a sanitary product such as a mask and cotton swab may be allowed to contain the MPM composition. In addition, detergents such as for residence, kitchen and cloth, which are for use in a lavatory, bath, kitchen, tableware, cloth or the like, may be allowed to contain the MPM composition. Moreover, a cosmetic product such as lotion or emulsion may be allowed to contain the MPM composition. Furthermore, a filter for exhaust of a car may be allowed to contain the MPM composition, and a filter of an air-conditioner may be allowed to contain the MPM composition.

Also, the MPM aqueous solution may be filled in a spray can so as to be used as an antibacterial and antiviral agent for residence, which is for use in, for example, a floor or wall in a house or the like, tiles of a table or the like installed in a house, and a fixture and furniture made of metal, plastic, glass, wood or the like in a house. In addition, the MPM aqueous solution may be filled in a spray can so as to be used as an antibacterial and antiviral agent for kitchen, or an antibacterial and antiviral agent for cloth, which is for use in a lavatory, bath, kitchen, cloth, or the like. Moreover, the MPM aqueous solution may be used as an antifungal agent. Note that because the MPM aqueous solution does not inhibit the effect of another ingredient such as a medical agent, and the antibacterial activity and antiviral activity of the MPM aqueous solution are not also inhibited by another medical agent or the like, as described above, the MPM aqueous solution may also be allowed to contain such another medical agent or the like.

Here, the MIC (minimum growth inhibitory concentration) of the MPM aqueous solution is indicated in Table 1, where the MPM composition is dissolved in water in which $VOSO_4$, $K_{11}H[(VO)_3(SbW_9O_{33})_2]$, $Na_9[SbW_9O_{33}]$, oxacillin and irgasan are combined at a molar ratio of 5.5:1:17.3:12.5:0.1 in the order.

TABLE 1

| Classification | Species | MIC (ppm) |
| --- | --- | --- |
| Gram positive bacterium | Staphylococcus aureus | 0.1 |
| | Streptococcus aureus | 10 |
| | Bacillus subtilis | 1 |
| Gram negative bacterium | Escherichia coli | 3 |
| | Proteus Vulgaris | 1 |
| | Salmonella typhi | 1 |
| | Shigella dysenteriae | 3 |
| | Salmonella choleraesuis | 1 |
| Eumycota | Trichophyton floccosum | 10 |
| | Epidermophyton floccosum | 10 |
| Fungus | Peonicillium citrinum | 10 |
| | Candida albicans | 10 |

As indicated in Table 1, even when the concentration of the MPM composition included in the MPM aqueous solution is low, the growth of microorganisms such as bacteria may be inhibited, and the MPM aqueous solution has a wide antibacterial spectrum. In other words, the MPM aqueous solution has an activity against wide bacterial species. Furthermore, the MPM aqueous solution has also an activity against MRSA (methicillin-resistant *Staphylococcus aureus*).

In addition, the MPM aqueous solution is stable as an aqueous solution, and thus the long term storage is also possible.

EXAMPLES

Hereinafter, a more specific description is made of the present invention with reference to the Examples.

Test for Inspection and Washing of Common Bacterium

Example 1-1

First of all, a towel as a specimen was washed, dewatered and rinsed with the use of a washing machine (150K washer).

The steps in which the washing machine was used were performed as indicated in Table 2. In short, a main washing was performed one time and a rinsing was performed three times, in each of the main washing and the second rinsing being added 2000 cc of sodium hypochlorite having a concentration of 12%. In addition, in the main washing were further added 1800 cc of synthetic detergent (Cosmo Clean) and 500 cc of TK2000 (alkaline auxiliary agent). In addition, in the third rinsing was added an MPM composition as 100 cc of an MPM aqueous solution including 25, 115, 1000, 100 and 0.6 μg/ml, of $VOSO_4$, $K_{11}H[(VO)_3(SbW_9O_{33})_2]$, $Na_9[SbW_9O_{33}]$, oxacillin and irgasan, respectively, the compounding ratio of which at a molar ratio was 5.5:1:17.3:12.5:0.1 in the order.

TABLE 2

| Step | Time (minutes) | Detergents etc. | Consumed amount |
|---|---|---|---|
| Main washing temperature 65° C. middle water level | 10 | Sodium hypochlorite(aq) Cosmo Clean TK2000 | 2000 cc 1800 cc 500 cc |
| Low speed dewatering | 1 | — | — |
| Rinsing 1 temperature 40° C. high water level | 3 | — | — |
| Low speed dewatering | 1 | — | — |
| Rinsing 2 high water level | 3 | Sodium hypochlorite(aq) | 2000 cc |
| Low speed dewatering | 1 | — | — |
| Rinsing 3 middle water level | 5 | MPM aqueous solution | 100 cc |
| High speed dewatering | 4.5 | — | — |

Subsequently, a Stomachere method was performed to yield an extract, which was then used as a sample. In short, into a sterilized polyethylene bag for Stomachere were put one towel and 100 ml of sterilized saline, which were treated in the Stomachere for approximately 3 minutes to yield an extract. As the towel used in the Stomachere method to yield the extract, three kinds of towels were used, including a towel just after the washing was performed, a towel stored at room temperature in a factory for one week from the washing, and a towel stored at room temperature in a factory for two weeks from the washing. In addition, for each condition, two specimens (towels) were subjected to the test for washing.

Then, 1 ml of the sample was collected and diluted 10 times in 4 to 5 stages with the use of a sterilized saline, and 1 ml of each of the diluted solutions was placed onto a sterilized Petri dish. To this was added approximately 15 ml of a standard agar medium that had been previously dissolved and kept at approximately 45° C. The mixture was rotated and mixed gently and cooled to solidify, and the solidified was multilayered with approximately 5 ml of an additional standard agar medium and settled.

After the solidified was reversed and cultured at 35° C. for two days, colonies occurred were counted and the number of bacterium was estimated by a calculation. The number of bacterium for the common bacterium that resulted from the sample cultured in the Petri dish for one specimen (towel), and the number of bacterium for the common bacterium that resulted from the sample cultured in the Petri dish for another specimen (towel) were indicated as A-1 and A-2 in Table 3, respectively.

Example 1-2

The same treatment as that in Example 1-1 was performed except that the amount of the MPM aqueous solution added in the third rinsing was 150 cc. In addition, the number of bacterium for the common bacterium that resulted from the sample cultured in the Petri dish for one specimen (towel), and the number of bacterium for the common bacterium that resulted from the sample cultured in the Petri dish for another specimen (towel) were indicated as B-1 and B-2 in Table 3, respectively.

TABLE 3

| | [Number of common bacterium]/g | | | |
|---|---|---|---|---|
| Result of bacterial inspection | A-1 | A-2 | B-1 | B-2 |
| Those brought into inspection institute on that day, stored at 35° C. for two days in inspection institute, cultured, followed by bacterial inspection | 72,000 | 91,000 | 58,000 | 47,000 |
| Those stored at room temperature for one week in factory from washing, then sent or brought into inspection institute, stored at 35° C. for two days in inspection institute, cultured, followed by bacterial inspection | 61,000 | 58,000 | 17,000 | 17,000 |
| Those stored at room temperature for two weeks in factory from washing, then sent or brought into inspection institute, stored at 35° C. for two days in inspection institute, cultured, followed by bacterial inspection | 55,000 | 59,000 | 31,000 | 28,000 |

It is apparent that the more amount of the MPM aqueous solution may suppress the growth of bacterium more, as indicated in Table 3. In addition, it is apparent that the bacteria decrease in the first one week. Moreover, the growth of bacterium is hardly found after the two weeks. Accordingly, an activity of the MPM composition against the common bacteria is demonstrated.

Test for Inspection and Washing of Virus

Example 2-1

The washing, rinsing and dewatering of a towel were performed with the use of a washing machine in the same way as Example 1-1. Thereafter, an influenza virus had been sprayed to the towel, and 1 hour after the influenza virus had been sprayed, a Stomachere method was performed to yield an extract, which was then used as a sample.

Then, 1 ml of the sample was collected and diluted 10 times in 4 to 5 stages with the use of sterilized dilution water, and 1 ml of each of the diluted solutions was placed onto a sterilized Petri dish. To this was added approximately 15 ml of a standard agar medium that had been previously dissolved and kept at approximately 45° C. The mixture was rotated and mixed gently and cooled to solidify, and the solidified was multilayered with approximately 5 ml of an additional standard agar medium and settled.

After the solidified was reversed and cultured at 35° C. for two days, the fluctuation of intercellular viral particles was observed through a fluorescence microscope, colonies occurred were counted, and the infectious titer of virus was estimated by a calculation. Note that four specimens were subjected to this manipulation and the corresponding results and mean values were indicated in Table 4.

Example 2-2

The same treatment as that in Example 2-1 was performed except that the amount of the MPM aqueous solution added in the third rinsing was 150 cc. Note that four specimens were subjected to this manipulation and the corresponding results and mean values were indicated in Table 4.

Comparative Example 2-1

The same treatment as that in Example 2-1 was performed except that the MPM aqueous solution was not added in the third rinsing. Note that four specimens were subjected to this manipulation and the corresponding results and mean values were indicated in Table 4.

TABLE 4

|  | Specimen number | Infectious titer of virus | Mean infectious titer of virus |
|---|---|---|---|
| Example 2-1 | 1 | $1.5 \times 10^3$ PFU/mL | $1.15 \times 10^3$ PFU/mL |
|  | 2 | $4 \times 10^2$ PFU/mL |  |
|  | 3 | $2.6 \times 10^3$ PFU/mL |  |
|  | 4 | $1 \times 10^2$ PFU/mL |  |
| Example 2-2 | 1 | $1.5 \times 10^2$ PFU/mL | $2.5 \times 10^2$ PFU/mL |
|  | 2 | $4.5 \times 10^2$ PFU/mL |  |
|  | 3 | $1.25 \times 10^2$ PFU/mL |  |
|  | 4 | $2.75 \times 10^2$ PFU/mL |  |
| Comparative Example 2-1 | 1 | $8.25 \times 10^4$ PFU/mL | $7.06 \times 10^4$ PFU/mL |
|  | 2 | $5.75 \times 10^4$ PFU/mL |  |
|  | 3 | $4.75 \times 10^4$ PFU/mL |  |
|  | 4 | $9.5 \times 10^4$ PFU/mL |  |

According to these results, an antiviral effect of the MPM composition is demonstrated such that the mean infectious titer of virus when the MPM composition is used becomes approximately 1/100 of that when the MPM composition is not used.

Test for Inspection and Washing of *Bacillus cereus*

Example 3-1

The washing, rinsing and dewatering of a towel were performed with the use of a washing machine in the same way as Example 1-1. Thereafter, based on 10 quantitative test, 10.1 bacterial solution absorption method in JIS L 1902:2008 of "Testing for antibacterial activity and efficacy on textile products", an antibacterial activity test for the towel as a specimen was performed. In the antibacterial activity test, one bacterial strain of *Baccilus cereus* IFO13494 was used. In addition, the specimen was not subjected to a high pressure steam sterilization (121° C., 15 minutes). Moreover, a towel was used as a control to which the MPM aqueous solution had not been added in the third rinsing.

The numbers of living bacterium in test pieces just after the inoculation of *Bacillus cereus* and after the culture at 37° C. for 18 hours were measured and indicated in Table 5.

TABLE 5

| Bacterium tested | Section | Test piece | Number of living bacterium per test piece | | |
|---|---|---|---|---|---|
|  |  |  | Measurement-1 | Measurement-2 | Measurement-3 |
| *Bacillus cereus* | Just after inoculation | Control | $1.9 \times 10^4$ | $1.9 \times 10^4$ | $2.0 \times 10^4$ |
|  | After culture at 37° C. for 18 hours | Specimen | $1.6 \times 10^{2*}$ | $1.9 \times 10^{2*}$ | $2.8 \times 10^{2*}$ |
|  |  | Control | $2.3 \times 10^6$ | $1.5 \times 10^6$ | $1.8 \times 10^6$ |

Control: standard textile (cotton)
Solution for preparation of bacterial solution: 1/20 concentration of Nutrient Broth
Method for measuring number of living bacterium: pour plate culturing method
*Bacterium that is not targeted for test is included Example 3-2

The same test as that in Example 3-1 was performed except that the type of bacterium used in the antibacterial activity test was *Becillus cereus* IFO13494 (spore). The result is indicated in Table 6.

TABLE 6

| Bacterium tested | Section | Test piece | Number of living bacterium per test piece | | |
|---|---|---|---|---|---|
|  |  |  | Measurement-1 | Measurement-2 | Measurement-3 |
| *Bacillus cereus* (spore) | Just after inoculation | Control | $1.7 \times 10^4$ | $1.5 \times 10^4$ | $1.9 \times 10^4$ |
|  | After culture at 37° C. for 18 hours | Specimen | $1.7 \times 10^4$ | $1.3 \times 10^4$ | $1.6 \times 10^4$ |
|  |  | Control | $2.8 \times 10^5$ | $1.8 \times 10^5$ | $1.6 \times 10^5$ |

Control: standard textile (cotton)
Solution for preparation of bacterial solution: 1/20 concentration of Nutrient Broth
Method for measuring number of living bacterium: pour plate culturing method According to the results as indicated in Tables 5 and 6, an effect of the MPM composition against *Bacillus cereus* is demonstrated such that the numbers of living bacterium of *Bacillus cereus* and *Bacillus cereus* (spore) when the MPM composition is used can be suppressed, compared to those when the MPM composition is not used.

Test for Inspection and Washing of MRSA

Example 4-1

The washing, rinsing and dewatering of a towel were performed with the use of a washing machine in the same way as Example 1-1, and a Stomachere method was performed to yield an extract, which was then used as a sample. The sample was diluted so as to produce specimen diluted solutions (100 times, 1000 times, and 10000 times diluted solutions from the specimen, which were prepared with 1/20 concentration of Nutrient Broth), into 10 mL of each of which 0.1 mL of a test bacterial solution was inoculated to produce a test solution.

Here, the test bacterial solution used was prepared such that a test bacterium (*Staphylococcus aureus*, IID 1677 (MRSA)) had been cultured in Nutrient Agar (Difco) at 37° C.±1° C. for 16 to 20 hours, and then suspended in 1/20 concentration of Nutrient Broth (Difco) so as to have the number of bacterium $10^6$ to $10^7$/mL.

The test solution was stored at 37° C.±1° C., and each of the test solutions at the starting time, 15 seconds later, 1 hour later and 24 hours later was immediately diluted 10 times on a medium for measuring the number of bacterium, allowing the number of living bacterium in the test solution to be measured. Note that as the medium for measuring the number of bacterium, a SCDLP agar medium (made by Nihon Pharmaceutical Co., Ltd.) was used, which would undergo cultivation according to a pour plate culturing method at 35° C.±1° C. for 2 days.

In addition, the same test was performed with the use of 1/20 concentration of the Nutrient Broth as a control. The numbers of living bacterium at the starting time, 1 hour later and 24 hours later were measured. The result is indicated in Table 7.

TABLE 7

| Bacterium tested | Subject | Concentration | Number of living bacterium (/ml) | | | |
|---|---|---|---|---|---|---|
| | | | Starting time* | 15 seconds later | 1 hour later | 24 hours later |
| MRSA | Specimen | 100 times diluted solution | $7.3 \times 10^4$ | $6.0 \times 10^4$ | $7.0 \times 10^4$ | $1.4 \times 10^3$ |
| | | 1000 times diluted solution | $7.3 \times 10^4$ | $5.4 \times 10^4$ | $6.1 \times 10^4$ | $5.0 \times 10^2$ |
| | | 10000 times diluted solution | $7.3 \times 10^4$ | $6.0 \times 10^4$ | $5.6 \times 10^4$ | $4.1 \times 10^4$ |
| | Control | — | $7.3 \times 10^4$ | *** | $6.7 \times 10^4$ | $1.0 \times 10^7$ |

*Number of living bacterium of control was measured just after inoculation of bacterial solution, this point being regarded as starting time
Control: 1/20 concentration of Nutrient Broth
*** Not applicable As indicated in Table 7, an effect of the MPM composition against MRSA is demonstrated such that the number of living bacterium of MRSA when the MPM composition is used can be suppressed, compared to that when the MPM composition is not used.

(Measurement of Discharged Water)

The discharged water including the MPM composition drained from the washing machine used in the process like Example 1-1 was collected in a treatment tank. As to the discharged water in this treatment tank, the individual items were measured, including the hydrogen-ion concentration (pH), chemical oxygen demand (COD), biochemical oxygen demand (BOD), suspended substance (SS), extractive substance in normal-hexane, number of coliform group, total nitrogen, and total phosphorus. Note that the measurement was performed three times in total with a difference in date or time. The result is indicated in Table 8.

TABLE 8

| Item | Unit | Result of measurement | | |
|---|---|---|---|---|
| | | Measurement-1 | Measurement-2 | Measurement-3 |
| Hydrogen-ion concentration (pH) | — | 7.8 (21° C.) | 7.9 (14° C.) | 8.0 (14° C.) |
| Chemical oxygen demand (COD) | mg/L | 16 | 15 | 37 |
| Biochemical oxygen demand (BOD) | mg/L | 4.8 | 1.7 | 5.8 |
| Suspended substance (SS) | mg/L | 9 | 3 | 10 |
| Extractive substance in normal-hexane | mg/L | 2 | Less than 1 | 1 |
| Number of coliform group | Groups/mL | Not detected | Not detected | Not detected |
| Total nitrogen | mg/L | 6.8 | 2.0 | 2.4 |
| Total phosphorus | mg/L | 1.9 | 3.5 | 10 |

| Item | Method for measuring (weighing) |
|---|---|
| Hydrogen-ion concentration(pH) | JIS 0102 12.1 |
| Chemical oxygen demand(COD) | JIS 0102 17 |
| Biochemical oxygen demand(BOD) | JIS 0102 21 and 32.3 |
| Suspended substance(SS) | Appendix table 9, No. 59 Notification from Ministry of Environment in 1971 |
| Extractive substance in normal-hexane | Appendix table 4, No. 64 Notification from Ministry of Environment in 1974 |
| Number of coliform group | No. 1 order for Enforcement of Building Standards Act from Ministry of Health and Welfare in 1962 |
| Total nitrogen | JIS 0102 45.1 |
| Total phosphorus | JIS 0102 46.3.1 |

As indicated in Table 8, the discharged water in the treatment tank satisfies the environmental standard, and does not have such an adverse effect on microorganisms (bacteria) as to deaden them in the treatment tank that performs a microbiological treatment method.

The invention claimed is:

1. A wet hand towel, having a substrate containing an aqueous solution in which a composition comprising $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol is dissolved, wherein compounds of $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol have the concentrations in the aqueous solution from 1 to 50 µg/mL, from 10 to 300 µg/mL, from 50 to 1500 µg/mL, from 5 to 200 µg/mL and from 0.01 to 3 µg/mL, respectively.

2. A method for producing a wet hand towel, comprising the steps of:
preparing a substrate; and
allowing the substrate to contain an aqueous solution in which a composition comprising $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol is dissolved, wherein compounds of $VOSO_4$, $K_{11}H[(VO)_3(SbW_9O_{33})_2]$, $Na_9[SbW_9O_{33}]$, oxacillin and 5-chloro-2-(2,4-dichlorophenoxy)phenol have the concentrations in the aqueous solution from 1 to 50 µg/mL, from 10 to 300 µg/mL, from 50 to 1500 µg/mL, from 5 to 200 µg/mL and from 0.01 to 3 µg/mL, respectively.

3. The method for producing a wet hand towel according to claim 2, comprising the step of
washing the substrate,
wherein the step of washing is performed before the step of allowing to contain.

* * * * *